US011192862B2

(12) United States Patent
Wilson et al.

(10) Patent No.: US 11,192,862 B2
(45) **Date of Patent: *Dec. 7, 2021**

(54) MICROCRYSTALLINE DIKETOPIPERAZINE COMPOSITIONS AND METHODS

(71) Applicant: MannKind Corporation, Westlake Village, CA (US)

(72) Inventors: Bryan R. Wilson, Brewster, NY (US); Joseph J. Guarneri, Stamford, CT (US); Marshall L. Grant, Newtown, CT (US)

(73) Assignee: MannKind Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,166

(22) Filed: Jul. 9, 2020

(65) Prior Publication Data

US 2020/0339520 A1 Oct. 29, 2020

Related U.S. Application Data

(63) Continuation of application No. 16/532,968, filed on Aug. 6, 2019, now Pat. No. 10,745,359.

(51) Int. Cl.

| | |
|---|---|
| ***C07D 241/08*** | (2006.01) |
| ***A61P 3/10*** | (2006.01) |
| ***A61K 9/14*** | (2006.01) |
| ***A61K 9/50*** | (2006.01) |
| ***B01D 1/18*** | (2006.01) |
| ***A61K 38/26*** | (2006.01) |
| ***A61K 38/28*** | (2006.01) |

(52) U.S. Cl.
CPC .............. *C07D 241/08* (2013.01); *A61K 9/14* (2013.01); *A61K 9/5015* (2013.01); *A61K 38/26* (2013.01); *A61K 38/28* (2013.01); *A61P 3/10* (2018.01); *B01D 1/18* (2013.01)

(58) Field of Classification Search
CPC ........... C07D 241/08; A61P 3/10; A61K 9/14; A61K 9/5015; A61K 38/26; A61K 38/28; B01D 1/18
See application file for complete search history.

(56) References Cited

FOREIGN PATENT DOCUMENTS

WO WO2007/033372 * 3/2007 ............... A61K 9/16

* cited by examiner

*Primary Examiner* — Trevor Love
(74) *Attorney, Agent, or Firm* — K&L Gates LLP; Louis C. Cullman; Hal Gibson

(57) ABSTRACT

Disclosed herein are DKP microcrystals made by an improved method where they do not irreversibly self-assemble into microparticles. The microcrystals can be dispersed by atomization and re-formed by spray drying into particles having spherical shell morphology. Active agents and excipients can be incorporated into the particles by spray drying a solution containing the components to be incorporated into microcrystalline diketopiperazine particles. In particular, the microcrystalline particle compositions are suitable for pulmonary drug delivery of one or more peptides, proteins, nucleic acids and/or small organic molecules.

9 Claims, 7 Drawing Sheets

FIG. 1A
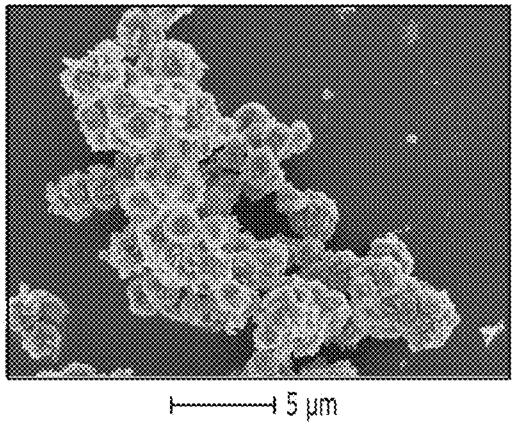
FIG. 1B
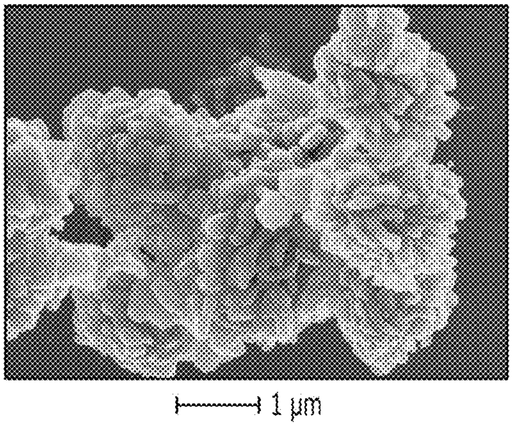
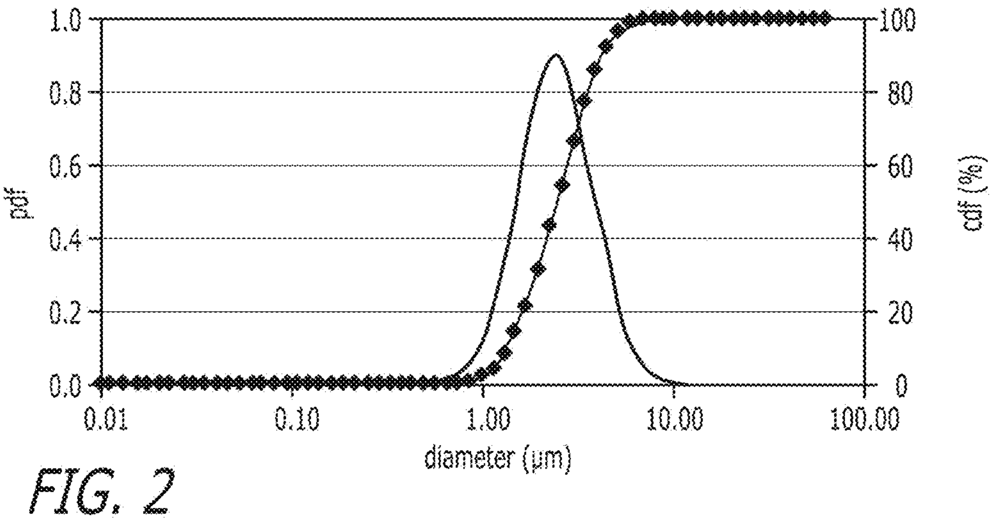
FIG. 2

FIG. 5
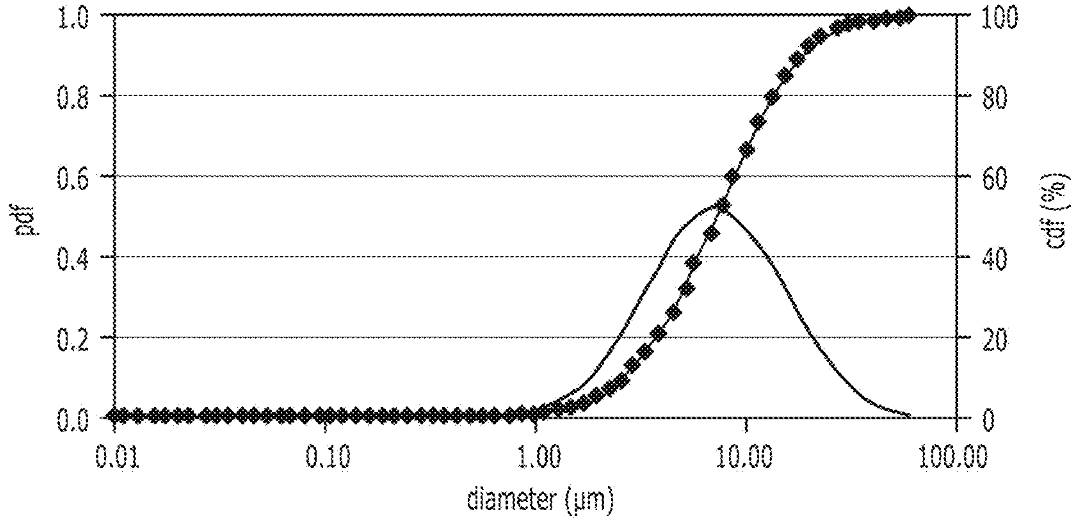
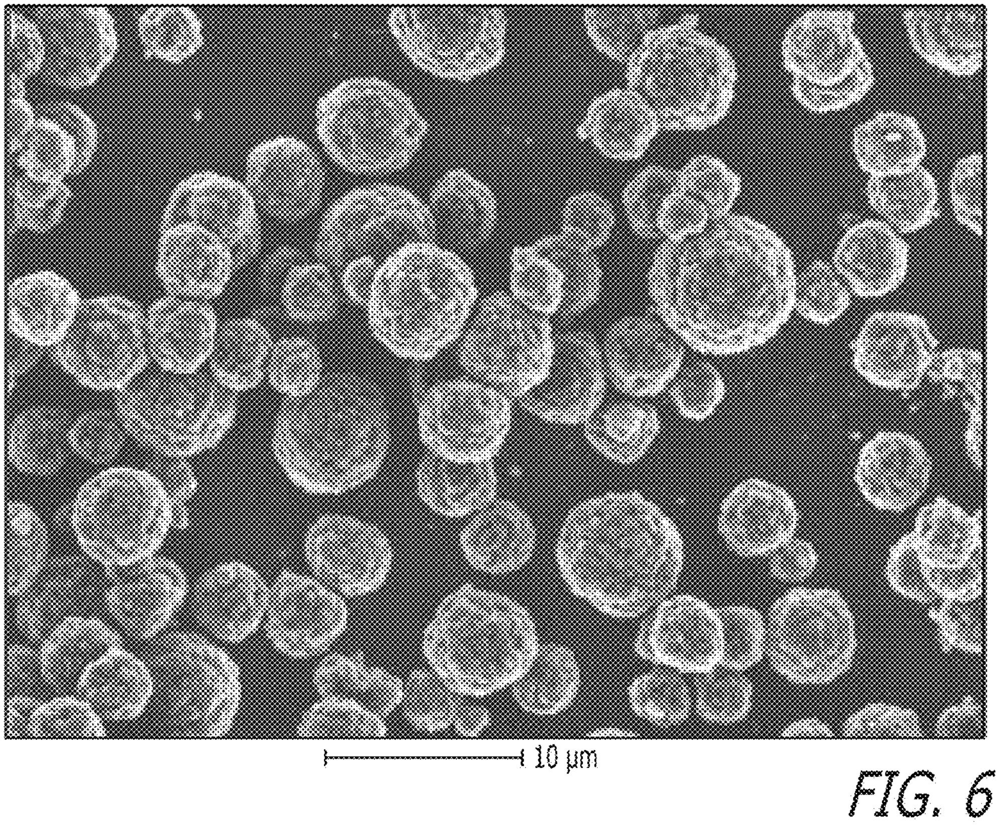
FIG. 6

MICROCRYSTALLINE DIKETOPIPERAZINE COMPOSITIONS AND METHODS

CROSS REFERENCE TO RELATED APPLICATIONS

This application is a continuation of U.S. patent application Ser. No. 16/532,968, filed Aug. 6, 2019, which is a divisional of U.S. patent application Ser. No. 14/774,311, filed Sep. 10, 2015, which is a 371 of PCT/US2014/029491, filed Mar. 14, 2014, which claims the benefit of U.S. Provisional Patent Application Ser. No. 61/800,520, filed Mar. 15, 2013, the contents of each of which is incorporated herein by reference in its entirety.

TECHNICAL FIELD

Disclosed herein are microcrystalline diketopiperazine (DKP) particles, compositions, methods of making the particles and method of using the particles. In particular, the particles can be used as a delivery system for drugs or active agents in the treatment of disease or disorders, for example, those of endocrine origin, including diabetes and obesity.

BACKGROUND

Delivery of drugs has been a major problem for many years, particularly when the compound to be delivered is unstable under the conditions encountered in the gastrointestinal tract when administered orally to a subject, prior to reaching its targeted location. For example, it is preferable in many cases to administer drugs orally, especially in terms of ease of administration, patient compliance, and decreased cost. However, many compounds are ineffective or exhibit low or variable potency when administered orally. Presumably this is because the drugs are unstable to conditions in the digestive tract or because they are inefficiently absorbed.

Due to the problems associated with oral drug delivery, drug delivery to the lungs has been explored. For example, typically drugs delivered to the lungs are designed to have an effect on the tissue of the lungs, for example, vasodilators, surfactants, chemotherapeutic agents or vaccines for flu or other respiratory illnesses. Other drugs, including nucleotide drugs, have been delivered to the lungs because they represent a tissue particularly appropriate for treatment, for example, for genetic therapy in cystic fibrosis, where retroviral vectors expressing a defective adenosine deaminase are administered to the lungs.

Drug delivery to the lungs for agents having systemic effects can also be performed. Advantages of the lungs for delivery of systemic agents include the large surface area and the ease of uptake by the lung's mucosal surface. Pulmonary drug delivery systems present many difficulties, for example, the use of propellants, and aerosolization of biological agents such as proteins and peptides can lead to denaturation, and excessive loss of the agent to be delivered. One other problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

Accordingly, there is room for improvement in the pulmonary delivery of drugs.

SUMMARY

The present disclosure provides improved microcrystalline particles, compositions, methods of making the particles, and methods that allow for improved delivery of drugs to the lungs for treating diseases and disorders in a subject. Embodiments disclosed herein achieve improved delivery by providing crystalline diketopiperazine compositions comprising microcrystalline diketopiperazine particles having high capacity for drug adsorption yielding powders having high drug content of one or more active agents. Powders made with the present microcrystalline particles can deliver increased drug content in lesser amounts of powder dose, which can facilitate drug delivery to a patient. The powders can be made by various methods including, methods utilizing surfactant-free solutions or solutions comprising surfactants depending on the starting materials.

Certain embodiments disclosed herein can comprise powders comprising a plurality of substantially uniform, microcrystalline particles, wherein the particles have a substantially hollow spherical structure and comprise a shell which can be porous, and comprises crystallites of a diketopiperazine that do not self-assemble.

Certain embodiments disclosed herein comprises powders comprising a plurality of substantially uniform, microcrystalline particles, wherein the particles have a substantially hollow spherical structure and comprise a shell which can be porous, and comprises crystallites of a diketopiperazine that do not self-assemble, and the particles have a volumetric median geometric diameter less than 5 μm.

In a particular embodiment herein, up to about 92% of the microcrystalline particles have a volumetric median geometric diameter of ≤5.8 μm. In one embodiment, the particle's shell is constructed from interlocking diketopiperazine crystals having one or more drugs adsorbed on their surfaces. In some embodiments, the particles can entrap the drug in their interior void volume and/or combinations of the drug adsorbed to the crystallites' surface and drug entrapped in the interior void volume of the spheres.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble; wherein the particles are formed by a method comprising the step of combining diketopiperazine having a trans isomer content ranging from about 45% to 65% in a solution and a solution of acetic acid without the presence of a surfactant and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble, and the particles have a volumetric mean geometric diameter less than equal to 5 μm; wherein the particles are formed by a method comprising the step of combining diketopiperazine in a solution and a solution of acetic acid without the presence of a surfactant and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In certain embodiments, a diketopiperazine composition comprising a plurality of substantially uniformly formed, microcrystalline particles is provided, wherein the particles have a substantially hollow spherical structure and comprise a shell comprising crystallites of a diketopiperazine that do not self-assemble, and the particles have a volumetric mean geometric diameter less than equal to 5 μm; wherein the particles are formed by a method comprising the step of combining diketopiperazine in a solution and a solution of acetic acid without the presence of a surfactant and without the presence of an active agent, and concurrently homogenizing in a high shear mixer at high pressures of up to 2,000 psi to form a precipitate; washing the precipitate in suspension with deionized water; concentrating the suspension and drying the suspension in a spray drying apparatus.

The method can further comprise the steps of adding with mixing a solution comprising an active agent or an active ingredient such as a drug or bioactive agent prior to the spray drying step so that the active agent or active ingredient is adsorbed and/or entrapped on or within the particles. Particles made by this process can be in the submicron size range prior to spray-drying.

In one embodiment, the composition can comprise microcrystalline particles comprising one or more active ingredients; wherein the active ingredients are peptides, proteins, nucleic acid molecules, small organic molecules, or combinations thereof. In embodiments wherein the active ingredient is a peptide, oligopeptide, polypeptide or protein, the peptide, oligopeptide, polypeptide or protein can be an endocrine hormone, a neurotransmitter, a vasoactive peptide, a receptor peptide, a receptor agonist or antagonist, and the like. In some embodiments, the endocrine hormone is insulin, parathyroid hormone, calcitonin, glucagon, glucagon-like peptide 1, oxyntomodulin, peptide YY, leptin, or an analog of said endocrine hormone. In embodiments, excipients can be incorporated into the particles by addition to one, another, or all feedstocks used in the spray drying step.

In one embodiment wherein the composition comprises insulin as the active ingredient, the compositions can contain insulin in amount up to, for example, 9 units or 10 units per milligram of powder to be delivered to a patient. In this embodiment, insulin can be delivered to a patient in amounts up to, for example, 100 units in a single inhalation using a dry powder inhaler. The compositions can be administered to a patient in need of insulin for the treatment of diabetes and/or hyperglycemia.

In an exemplary embodiment, the crystalline diketopiperazine composition comprises a diketopiperazine of the formula 3,6-bis(N-X-4-aminoalkyl)-2,5-diketopiperazine, wherein alkyl denotes an alkyl containing 3 to 20 carbon atoms, including propyl, butyl, pentyl, hexyl, heptyl and the like; and the formula is, for example, 3,6-bis(N-X-4-aminobutyl)-2,5-diketopiperazine, wherein X is selected from the group consisting of fumaryl, succinyl, maleyl, malonyl, and glutaryl, or a salt thereof. In a particular embodiment, the diketopiperazine is 3,6-bis(N-fumaryl-4-aminobutyl)-2,5-diketopiperazine having the formula:

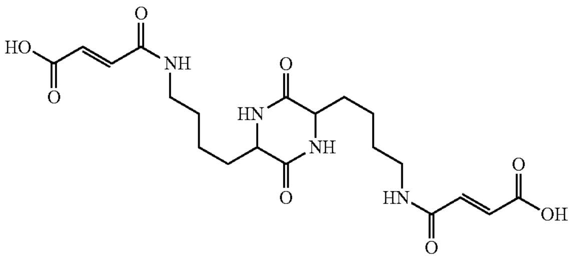 [SMILES: O=C(O)/C=C/C(=O)NCCCCC1NC(=O)C(CCCCNC(=O)/C=C/C(=O)O)NC1=O]

In various embodiments, a method of making dry powders comprising microcrystalline particles suitable for pulmonary administration is provided; wherein the method can be carried out using surfactant-free solutions, or solutions comprising a surfactant. In one aspect the diketopiperazine comprises a trans isomer content ranging from about 45% to 65%.

Certain embodiments disclosed herein include methods of producing dry powders comprising crystalline diketopiperazine microparticles from starting materials comprising free acid diketopiperazines.

Certain embodiments disclosed herein include methods of producing dry powders comprising crystalline diketopiperazine microparticles from starting materials comprising diketopiperazine salts.

In one embodiment, the method comprises:

dissolving a diketopiperazine in aqueous ammonia to form a first solution;

feeding the first solution and a second solution comprising about 10.5% acetic acid concurrently to a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming particles by spray-drying into a dry powder comprising the microcrystalline particles having substantially hollow spheres.

In another embodiment, the method comprises:

dissolving a diketopiperazine in aqueous sodium hydroxide and optionally a surfactant to form a first solution;

feeding the first solution and a second solution comprising about 10.5% acetic acid, and optionally a surfactant, concurrently to a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter and comprising a trans isomer content ranging from about 45% to 65%;

atomizing the suspension under an air or gas stream; and reforming particles by spray-drying into a dry powder comprising the microcrystalline particles having substantially hollow spheres.

In one embodiment, the method comprises:

dissolving a diketopiperazine in aqueous ammonia to form a first solution;

feeding the first solution and a second solution comprising about 10.5% acetic acid concurrently to a high shear mixer at an approximate pH of less than 6.0 under high pressure to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming particles by spray-drying into a dry powder comprising the microcrystalline particles having substantially hollow spheres.

The method can further comprise the step of adding a third solution to the diketopiperazine crystallite suspension prior to atomizing the suspension; wherein the solution contains a drug or a pharmaceutically active ingredient, and the atomizing step can be performed using an external mixing 2-fluid nozzle into a spray dryer fitted with a high efficiency cyclone separator under air or gas, including nitrogen gas.

In certain embodiments, the particles in suspension have a particle size distribution as a bimodal curve as measured by laser diffraction; wherein a first peak of particles has an average particle size of about 0.2 μm to about 0.4 μm, and a second peak of particles having an average size of about 2.1 μm to about 2.4 μm in diameter.

In some embodiments, the step of atomizing the suspension uses a nitrogen stream of about 700 liters of nitrogen per hour as the process gas, and the nozzle temperature can be kept at about 25° C.

Microcrystalline particles formed by the method above do not self-assemble when suspended in a solution, such as water or other aqueous-based solvent. In a particular embodiment, the method comprises a diketopiperazine of the formula 3,6-bis(N-X-4-aminobutyl)-2,5-diketopiperazine, wherein X is selected from the group consisting of fumaryl, succinyl, maleyl, malonyl, and glutaryl. In a specific embodiment, the method comprises homogenizing in a high shear mixer a solution of a diketopiperazine, wherein the diketopiperazine is 3,6-bis(N-fumaryl-4-aminobutyl)-2,5-diketopiperazine, or a salt thereof, including, disodium, dipotassium, magnesium, calcium, and dilithium salts.

In an embodiment, a crystalline diketopiperazine composition comprising a plurality of microcrystalline particles substantially uniform in size is obtained as a product of the spray drying step.

In an embodiment, a crystalline diketopiperazine composition comprising a plurality of microcrystalline particles with a bimodal size distribution is obtained as a product of the crystallite formation step.

When a disruption step is used, the larger species of the bimodal distribution can be shifted to smaller sizes.

Certain embodiments comprise a method of forming microcrystalline particles of a diketopiperazine acid for making dry powders carrying large drug content comprises using a salt of a diketopiperazine as a starting compound, including, 3,6-bis(N-fumaryl-4-aminobutyl)-2,5-diketopiperazine disodium salt, the method comprises:

dissolving a diketopiperazine salt in water comprising a surfactant in an amount from about 0.2% to about 6% (w/w) to form a first solution;

combining the first solution with a second solution comprising from about 8% to about 12% (w/w) acetic acid concurrently in a high shear mixer at an approximate pH of less than 6.0 under high pressure;

homogenizing the first solution and second solution to form a suspension comprising crystallites of the diketopiperazine in the suspension, wherein the suspension has a bimodal distribution of crystallites having particle sizes ranging from about 0.05 μm to about 10 μm in diameter;

atomizing the suspension under an air or gas stream; and reforming the particles by spray-drying into a dry powder comprising microcrystalline particles of the diketopiperazine acid having substantially hollow spheres.

In a specific embodiment, microcrystalline particles can be made by a process comprising, preparing a first solution comprising a diketopiperazine in water, for example, 3,6-bis(N-fumaryl-4-aminobutyl)-2,5-diketopiperazine disodium salt and a surfactant such as polysorbate 80; preparing a second solution comprising acetic acid at a concentration about 10.5% (w/w) and a surfactant at a concentration of about 0.5% (w/w); mixing the first solution and the second solution in a high shear mixer to form a suspension; optionally testing the suspension to determine the particle size distribution so that the suspension comprises a bimodal particle size distribution, with particles ranging in size from about 0.2 μm to about 10 μm in diameter, wherein a first peak of particles have an average diameter of about 0.4 μm and a second peak of particle have an mean diameter of about 2.4 μm, and spray-drying the suspension to obtain a dry powder.

Certain embodiments can comprise a disruption step to reduce the size of the larger-sized population in the bimodal distribution, for example utilizing sonication, stirring, or homogenization. In embodiments the disruption step can be performed prior to atomizing the suspension.

In embodiments herein, the method for making the microcrystalline diketopiperazine particles can further include a wash step using deionized water. In one embodiment, the atomizing step can be performed, for example, using an external mixing 2-fluid nozzle into a spray dryer fitted with a high efficiency cyclone separator.

The method can further comprise the step of adding a solution comprising one or more active agents to the suspension prior to dispersing and/or spray drying, wherein the active agent is a peptide, an oligopeptide, a polypeptide, a protein, a nucleic acid molecule, or a small organic molecule. The peptides can be endocrine hormones, including insulin, parathyroid hormone, calcitonin, glucagon, glucagon-like peptide 1, oxyntomodulin, peptide YY, leptin, or an analog of said endocrine hormone and the like. The method can optionally comprise the step of adding a solution comprising a surfactant, and/or a pharmaceutically acceptable carrier, including amino acids such as leucine, isoleucine, and/or monosaccharides, disaccharides, or oligosaccharides, such as lactose, trehalose, and the like, or sugar alcohols, including, mannitol, sorbitol, and the like.

In another embodiment, a composition comprising more than one active agent can be made using the present method. The method of making such composition comprises the steps of making microcrystalline diketopiperazine particles comprising more than one active agent wherein each active agent/ingredient is processed separately in a solution and added to separate suspensions of diketopiperazine particles and solution conditions are changed to promote adsorption of the active agent onto the surfaces of the crystallites, then the two or more separate suspensions comprising the active agents are blended prior to dispersing and spray-drying the particles. In a variant procedure, the blend includes a suspension containing diketopiperazine particles without active agent, for example in order to achieve a lower overall content of the active agent. In an alternate embodiment, the one or more independent solutions containing a single active agent can be combined with a single suspension comprising the diketopiperazine particles prior to dispersing and spray-drying the particles. The resultant dry powder comprises a composition comprising two or more active ingredients. In these embodiments, the amount of each ingredient in the composition can be controlled depending on the need of the patient population to be treated.

In another embodiment, the dry powder comprises a composition comprising 3,6-bis(N-X-4-aminobutyl)-2,5-diketopiperazine, wherein X is fumaryl and the composition comprises substantially homogeneous microcrystalline particles comprising a drug; wherein the particles are substantially spherical in shape having a substantially hollow core and the crystallites form a shell of the sphere. In another embodiment, the dry powders comprise a diketopiperazine of the formula 3,6-bis(N-X-4-aminobutyl)-2,5-diketopiperazine and a drug, wherein the drug is a peptide, wherein the peptide can be of various peptide lengths, molecular sizes or masses, including; insulin, glucagon-like peptide-1, glucagon, exendin, parathyroid hormone, calcitonin, oxyntomodulin, and the like.

Further embodiments include drug delivery systems comprising an inhaler with or without a cartridge, wherein the cartridge is a unit dose dry powder medicament container, for example, a cartridge, and a powder comprising the particles disclosed herein and an active agent. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 ($\sqrt{kPa}$)/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system is configured to provide a single dose by discharging powder from the inhaler as a continuous flow, or as one or more pulses of powder delivered to a patient. In some embodiments disclosed herewith, the dry powder inhaler system comprises a predetermined mass flow balance within the inhaler, wherein the inhaler conduits are designed to have varied flow distribution during an inhalation. For example, a flow balance of approximately 10% to 70% of the total flow exiting the inhaler and into the patient is delivered by one or more dispensing ports, which airflow passes through an air conduit designed with an area for containing a powder formulation, and wherein approximately 30% to 90% air flow is generated from other conduits of the inhaler during an inhalation maneuver. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 50 mg. In certain embodiments, an inhalation system as described above can emit a respirable fraction/fill of a powder dose at percentages greater than 40% in a single inhalation, greater than 50%, greater than 60%, or greater than 70%.

In certain embodiments, drug delivery systems comprising inhalers can comprise inhalers particularly suited for use with the morphology of the particles comprising the dry powder, such as for example a crystalline or amorphous morphology.

In particular embodiments, an inhalation system is provided comprising a dry powder inhaler, a dry powder formulation comprising microcrystalline particles of fumaryl diketopiperazine having an FDKP trans isomer content between 45% and 65% and one or more than one active agents. In some aspects of this embodiment of the inhalation system, the dry powder formulation is provided in a unit dose cartridge. Alternatively, the dry powder formulation can be preloaded in the inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 μm. The inhalers can discharge greater than 85% of a powder medicament contained within a container during dosing. In certain embodiments, the inhalers can discharge greater than 85% of a powder medicament contained in a single inhalation. In one embodiment, the inhalers can discharge greater that 90% of the cartridge contents or container contents in less than 3 seconds at pressure differentials between 2 and 5 kPa with fill masses ranging up to 30 mg.

Embodiments disclosed herein also include methods. In one embodiment, a method of treating an endocrine-related disease or disorder comprising administering to a person in need thereof a dry powder formulation comprising FDKP microcrystalline particles comprising an FDKP that can have a trans isomer content of about 45 to about 65% and a drug suitable to treat said disease or disorder wherein the microparticles are produced by the present methods. One embodiment includes a method of treating an insulin-related disorder comprising administering a dry powder comprising microcrystalline particles of FDKP described above to a person in need thereof. The method comprises administering to a subject a dry powder formulation comprising microcrystalline particles of fumaryl diketopiperazine having a trans isomer content ranging from about 45% to 65%, which are particles are hollow spheres and do not contain any surfactant. In various embodiments an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises oxyntomodulin, peptide YY, leptin, oxytocin, glucagon, an exendin, GLP-1 analogs thereof or combinations thereof.

Another embodiment disclosed herein includes a method of delivering a peptide including, GLP-1, oxyntomodulin, peptide YY, oxytocin, insulin to a patient in need thereof comprising administering a dry powder comprising diketopiperazine microcrystalline particles disclosed herein to the deep lung by inhalation of the dry powder by the patient. In aspects of this embodiment, particular features of an inhaler system are specified.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

FIGS. 1A and 1B are a scanning electron micrographs (SEM) of fumaryl diketopiperazine particles comprising insulin and showing the solid compositions of the particles lyophilized at low (1A) and high magnification (1B).

FIG. 2 depicts a graphic representation of the particle size distribution of the particles depicted in FIGS. 1A and 1B as measured by the probability density function (pdf, left y-axis) and cumulative distribution function (cdf, right y-axis) scale.

FIG. 5 depicts a graphic representation of the lyophilized particle size distribution in suspension as depicted in FIG. 4 formed without surfactant and showing an increase in particle size as measured by the probability density function (pdf, left y-axis) scale and cumulative distribution function (cdf, right y-axis) scale.

FIG. 6 depicts an SEM (at 2500×) of a claimed embodiment showing microcrystalline particles made from surfactant-free solutions which were spray-dried.

DETAILED DESCRIPTION

Figure 3:
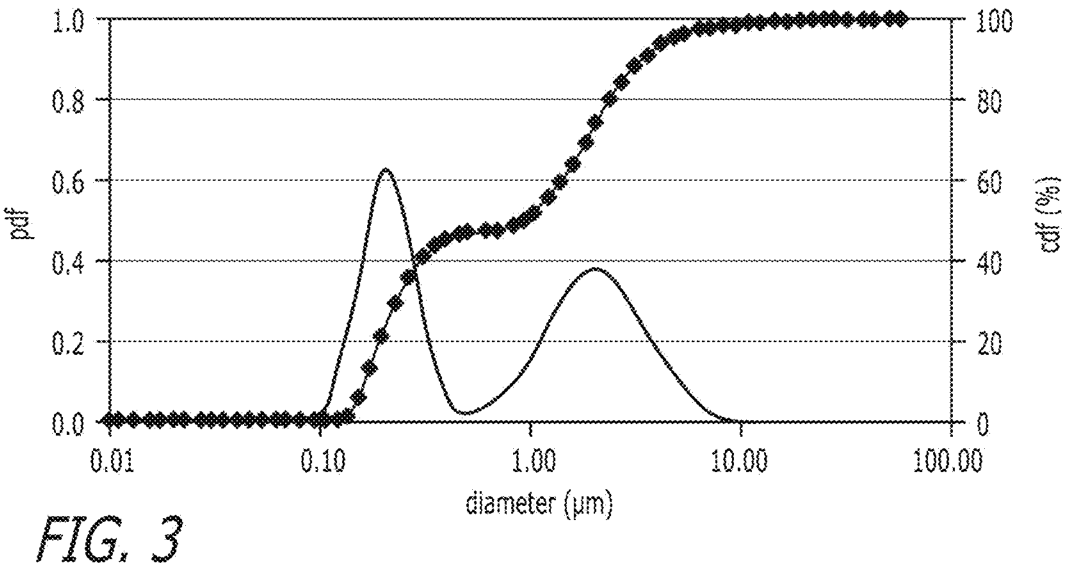
FIG. 3 depicts a graphic representation of the particle size distribution of particles obtained from an embodiment prepared from a suspension wherein the microcrystalline particles are formed without surfactant in any of the solutions used. The graph shows a typical bimodal distribution of the microcrystalline particles as measured by the probability density function (pdf, left y-axis) scale and cumulative distribution function (cdf, right y-axis) scale.

As stated, drug delivery to the lungs offers many advantages. It is difficult to deliver drugs into the lungs, however, due to problems in transporting the drugs past natural physical barriers in a uniform volume and weight of the drug. Disclosed herein are crystalline diketopiperazine compositions, dry powders and methods of making the particles. The crystalline composition and dry powder therefrom comprise diketopiperazines microcrystalline particles, which are substantially uniformly defined spheres comprising a shell comprising crystallites of the diketopiperazine and a core. In certain embodiments the core can be hollow. In one embodiment, the diketopiperazine has a defined trans isomer content which can be beneficial to the particles as drug delivery agents, methods of making the particles and methods of treatment using the particles. The particles disclosed herein have higher capacity for carrying and delivering drug content to the patient in smaller doses than standard, prior art particles.

As used herein, an “analog” includes compounds having structural similarity to another compound. Thus, compounds having structural similarity to another (a parent compound) that mimic the biological or chemical activity of the parent compound are analogs. There are no minimum or maximum numbers of elemental or functional group substitutions required to qualify a compound as an analog provided the analog is capable of mimicking, in some relevant fashion, either identically, complementarily or competitively, with the biological or chemical properties of the parent compound. In some instances an analog comprises a fragment of the parent compound either in isolation or linked to another molecule and may contain other alterations as well. Analogs of the compounds disclosed herein may have equal, lesser or greater activity than their parent compounds.

As used herein, the term “microparticle” refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the “respirable fraction” (RF), generally accepted to be those particles with an aerodynamic diameter of about 0.5 to about 5.7 microns, though some references use somewhat different ranges, as measured using standard techniques, for example, with an Andersen Cascade Impactor. Other impactors can be used to measure aerodynamic particle size such as the NEXT GENERATION IMPACTOR™ (NGI™, MSP Corporation), for which the respirable fraction is defined by similar aerodynamic size, for example $<6.4$ μm. In some embodiments, a laser diffraction apparatus is used to determine particle size, for example, the laser diffraction apparatus disclosed in U.S. patent application Ser. No. 12/727,179, filed on Mar. 18, 2010, which is incorporated herein in its entirety for its relevant teachings, wherein the volumetric median geometric diameter (VMGD) of the particles is measured to assess performance of the inhalation system. For example, in various embodiments cartridge emptying of ≥80%, 85%, or 90% and a VMGD of the emitted particles of ≤12.5 μm, 7.0 μm, 5.8 μm or 4.8 μm can indicate progressively better aerodynamic performance. Embodiments disclosed herein show that FDKP particles with a trans isomer content of between about 45% to about 65% exhibit characteristics beneficial to delivery of drugs to the lungs such as improved aerodynamic performance.

Respirable fraction on fill (RF/fill) represents the % of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of particle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes <5.8 μm as measured using standard techniques.

As used herein, the term "dry powder" refers to a fine particulate composition that is not suspended or dissolved in a propellant, carrier, or other liquid. It is not meant to necessarily imply a complete absence of all water molecules.

Specific RF/fill values can depend on the inhaler used to deliver the powder. Powders generally tend to agglomerate and certain crystalline DKP particles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary. However, optimal RF/fill as a function of isomeric content will be the same from inhaler to inhaler.

As used herein, the term "about" is used to indicate that a value includes the standard deviation of the measurement for the device or method being employed to determine the value.

As used herein, the term "surfactant-free" is used to indicate that no surfactant was present in any of the reagents, including, solutions, and/or suspensions used in the process of making the microcrystalline particles.

As used herein, the term "crystallite" is used to refer to the integral crystalline units of a diketopiperazine particle, which can have varying sizes.

As used herein, "microcrystalline particles" comprise crystallites of a diketopiperazine and have a particle size distribution of from 0.05 μm to about 100 μm, as measured by laser diffraction having particles sizes of less than 50 μm, less than 20 μm, or less than 10 μm in diameter. In an embodiment the crystallites can range in size from 0.01 to 1 μm.

Diketopiperazines

One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

Formula 1

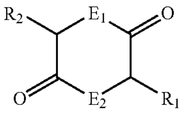

These 2,5-diketopiperazines have been shown to be useful in drug delivery, particularly those bearing acidic $R_1$ and $R_2$ groups as described in, for example, U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery. Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders the microparticles can be delivered by inhalation to specific areas of the respiratory system, including the lungs.

Such prior art microparticles are typically obtained by pH-based precipitation of the free acid (or base) resulting in self-assembled microparticles comprised of aggregated crystalline plates with a roseate morphology. The stability of the particle can be enhanced by small amounts of a surfactant, such as polysorbate-80, in the DKP solution from which the particles are precipitated (see for example U.S. Pat. No. 7,799,344, entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Methods of solvent removal include lyophilization and spray drying (see for example U.S. Pat. No. 8,039,431 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The particles disclosed herein are distinct from the prior art particles in that they are physically, and morphologically distinct entities and are made by an improved method. The present disclosure refers to FDKP to be understood as the free acid or the dissolved anion.

Other prior art particles are obtained by spray drying DKP solutions to obtain particles of the amorphous DKP salts typically with a collapsed-spherical morphology such as those disclosed in U.S. Pat. Nos. 7,820,676 and 8,278,308, entitled "Diketopiperazine salts for drug delivery and related methods."

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, "Catalysis of Diketopiperazine Synthesis," which is also incorporated by reference herein for its teachings regarding the same.

Fumaryl diketopiperazine 3,6-bis(N-fumaryl-4-aminobutyl)-2,5-diketopiperazine; FDKP) is one preferred diketopiperazine for pulmonary applications:

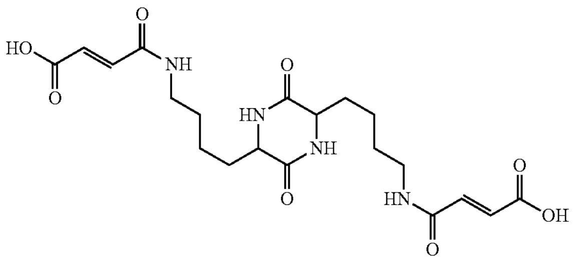 [SMILES: O=C(O)/C=C/C(=O)NCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble into microparticles under acidic conditions. The particles dissolve readily under physiological conditions where the pH is neutral. As noted, microparticles having a diameter of between about 0.5 and about 10 μm can reach the lungs, successfully passing most of the natural barriers. Particles in this size range can be readily prepared from FDKP.

FDKP possesses two asymmetric centers in the diketopiperazine ring. FDKP is manufactured as a mixture of geometric isomers that are identified as "cis-FDKP" and "trans-FDKP" according to the arrangement of side chains relative to the central "ring" of the diketopiperazine. The R,R and S,S enantiomers have the propenyl(amidobutyl) "side arms" projecting from the same planar side of the diketopiperazine ring (A and B below) and are thus referred to as the cis isomers while the R,S compound has the "side arms" projecting from opposite planar sides of the diketopiperazine ring (C below) and is referred to as the trans isomer.

A

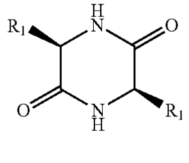

-continued

B

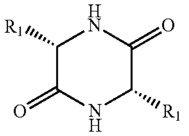

C

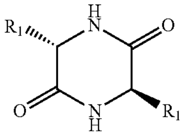

FDKP microparticle powders with acceptable aerodynamic performance, as measured by RF/fill with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same, have been produced from FDKP with a trans isomer content ranging from about 45 to about 65%. Particles with isomer content in this range also perform well with high efficiency inhalers such as those disclosed in U.S. Pat. No. 8,499,757 entitled, "A Dry Powder Inhaler and System for Drug Delivery," filed on Jun. 12, 2009, U.S. Pat. No. 8,424,518 entitled "Dry Powder Inhaler and System for Drug Delivery," filed on Jun. 12, 2009, U.S. patent application Ser. No. 13/941,365 entitled "Dry Powder Drug Delivery System and Methods," filed Jul. 12, 2013, and U.S. patent application Ser. No. 12/717,884, entitled, "Improved Dry Powder Drug Delivery System," filed on Mar. 4, 2010, which disclosures are herein incorporated by reference for their teachings regarding the same. Powders comprising microparticles containing more than 65% trans-FDKP tend to have lower and more variable RF/fill. Trans isomer-enriched microparticles of FDKP have altered morphology and also lead to viscous suspensions which are difficult to process.

Formulations of FDKP microparticles having a trans isomer content of about 45% to about 65% provide powders with acceptable aerodynamic properties as disclosed in U.S. Pat. No. 8,227,409, which disclosures are incorporated herein by reference for its teachings regarding the same. Formulations of FDKP particles having a defined specific surface area less than 67 $m^2/g$ also provide dry powders for inhalation with acceptable aerodynamic properties as disclosed in U.S. Pat. No. 8,551,528 entitled "Diketopiperazine Microparticles with Defined Specific Surface Areas" filed Jun. 11, 2010, which disclosure is incorporated herein by reference for its teachings regarding the same. These FDKP powders, however, tend to be cohesive and the inhaler is designed to overcome this characteristic.

It is thus desirable to produce diketopiperazine powders having a particle composition which is less cohesive, which would allow more effective drug delivery and less inhaler design around. The present disclosure ascertains that the present method of making microcrystalline particles of diketopiperazine as exemplified by FDKP and FDKP disodium salt provides microcrystalline dry powders with acceptable aerodynamic performance which powders are less cohesive, differ in density, have an alternate physical structure that does not self assemble in suspension and provide increased capacity for drug content, including delivering one or more active agents, which was not anticipated.

It was determined that improved consistency in homogeneity of the particles could be obtained with a different process for making the diketopiperazine microparticles. The present methods for making the compositions, and compositions comprising the present microcrystalline diketopiperazine particles provide dry powders for pulmonary inhalation with beneficial physical and morphological aerodynamic characteristics.

Selection and Incorporation of Active Agents

In exemplary embodiments comprising FDKP, at least as long as the microcrystalline particles described herein retain the above isomer content, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. Pat. No. 7,799,344, entitled "Method of Drug Formulation based on Increasing the Affinity of Crystalline Microparticle Surfaces for Active Agents," which is incorporated by reference herein for its teachings regarding the same. U.S. Pat. No. 7,803,404, entitled "Method of Drug Formation based on Increasing the Affinity of Active Agents for Crystalline Microparticle Surfaces" describes methods for promoting adsorption of active agents onto microparticles. U.S. Pat. No. 7,803,404 is also incorporated by reference herein for its teachings regarding the same. These teachings can be applied to the adsorption of active agent to crystallites in suspension, for example, prior to spray drying.

The microcrystalline particles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), $F(ab)_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents including opioid agonist and antagonists, hormones, anticoagulants, immunomodulating agents, cytotoxic agents, antibiotics, antiviral agents, antigens, infectious agents, inflammatory mediators, hormones, cell surface receptor agonist and antagonists, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-I2, LTB receptor blockers including LY29311, BIIL 284 and CP105696; triptans such as sumatriptan and palmitoleate, insulin and analogs thereof, growth hormone and analogs thereof, parathyroid hormone (PTH) and analogs thereof, parathyroid hormone related peptide (PTHrP), ghrelin, obestatin, enterostatin, granulocyte macrophage colony stimulating factor (GM-CSF), amylin, amylin analogs, glucagon-like peptide 1 (GLP-1), clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, analgesics, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide; and analogs of the active agents.

The drug content to be delivered on microcrystalline particles formed from FDKP or FDKP disodium salt can typically be greater than 0.01% (w/w). In one embodiment, the drug content to be delivered with the microcrystalline particles can be from about 0.01% (w/w) to about 75% (w/w); from about 1% to about 50% (w/w), from about 10% (w/w) to about 30% (w/w), or from about 10% to about 20% (w/w). In one embodiment, for example, if the drug is insulin, the present microparticles typically comprise approximately 10% to 45% (w/w), or from about 10% to about 20% (w/w) insulin. In certain embodiments, the drug content of the particles can vary depending on the form and size of the drug to be delivered. In an embodiment wherein GLP-1 is used as an active agent, the GLP-1 content can be up to 40% (w/w) of the powder content.

In an embodiment, a composition comprising more than one active agent can be made using the present method by adsorption, for example by binding the active agent to the crystallites before forming the dry powder.

In an embodiment, a composition comprising more than one active agent can be made using the present method by entrapping the active agent between and amongst the crystallites, for example by spray drying the material, without first adsorbing the active agent to the crystallites.

The method of making such composition can comprise the steps of making microcrystalline diketopiperazine particles comprising more than one active agents; wherein each active agent/ingredient is processed separately in a solution and added to separate suspensions of diketopiperazine particles, then the two or more separate suspensions comprising the active agents are blended prior to dispersing and spray-drying the particles.

In certain embodiments, crystallites can be mixed with a solution comprising one or more active agents.

In certain embodiments, crystallites can be mixed with a solution comprising one or more active agents wherein solution conditions are changed to promote adsorption of the active agent on to the crystallite surface.

Each of multiple active agents can be adsorbed to a separate aliquot or species of crystallites. The aliquot-adsorbed crystallites can then be mixed together and spray dried. Alternatively, an aliquot can contain no active agent so as to adjust the overall content of the active agent in the dry powder without altering the conditions used to adsorb the active agent on to the crystallites.

In an alternate embodiment, the one or more independent solutions containing a single active agent can be combined with a suspension comprising the diketopiperazine particles prior to dispersing and spray-drying to reform particles. The resultant dry powder composition comprises two or more active ingredients. In this embodiment, the amount of each ingredient can be controlled in the composition depending on the need of the patient population to be treated.

As is evident from the foregoing disclosure, microparticles of embodiments disclosed herein can take many different forms and incorporate many different drugs or active agents.

EXAMPLES

The following examples are included to demonstrate embodiments of the disclosed microcrystalline diketopiperazine particles. It should be appreciated by those of skill in the art that the techniques disclosed in the examples which follow represent techniques developed by the inventors to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the scope of the invention.

Example 1

Manufacture of Standard FDKP Microparticles

A prior art manufacturing process was used to produce FDKP microparticles for comparison purposes as standard particles as disclosed in U.S. Pat. Nos. 7,799,344; 7,803,404 and 8,227,409, which disclosures are incorporated herein by reference for their teachings of the relevant subject matter. In summary, the typical FDKP particle formation process, feed solutions of FDKP and acetic acid, each containing 0.05% (w/w) polysorbate 80 (PS80), are combined in a high shear mixer. Table 1 below shows the components for the FDKP and insulin stock solutions.

TABLE 1

| 10.5% Acetic Acid Solution filtered through 0.2 μm membrane | |
|---|---|
| Component | wt % |
| DI Water | 89.00 |
| GAA | 10.50 |
| 10% Polysorbate 80 | 0.50 |

TABLE 2

| 2.5% FDKP Solution filtered through 0.2 μm membrane | |
|---|---|
| Component | wt % |
| DI Water | 95.40 |
| FDKP | 2.50 |
| $NH_4OH$ | 1.60 |
| 10% Polysorbate 80 | 0.50 |

A concentrated insulin stock solution can be prepared with 1 part insulin and 9 parts about 2% wt acetic acid. The insulin stock can be added gravimetrically to the suspension to obtain a load of about 11.4% wt. The insulin-containing suspension can be mixed at least about 15 minutes, and then titrated with about 14 to about 15 wt % aqueous ammonia to a pH of about 4.5 from an initial pH of about 3.5. The suspension can be flash-frozen in liquid nitrogen to form pellets using a cryogranulator, for example, as disclosed in U.S. Pat. No. 8,590,320, which disclosure is incorporated herein by reference in its entirety, and lyophilized to yield the bulk insulin-loaded FDKP microparticles, which form small crystals or clusters that self-assemble into FDKP particles with an open structure as seen in FIGS. 1A and 1B.

Samples of particles formed were studied to measure the size distribution of these particles in suspension and the results are shown in FIG. 2. The data in FIG. 2 show a graphic representation of the particle size distribution measurements which are plotted in logarithmic scale as the probability density function (pdf, left y-axis) and the cumulative distribution function (cdf, right y-axis). The data show that the particles in suspension have a size distribution in a single peak which ranges from about 1.0 to about 10 μm in diameter centered on or about 2 μm.

Manufacture of Microcrystalline FDKP Particles a 2.5% (w/w) FDKP was dissolved in a basic solution of aqueous ammonia (1.6% ammonia). A 10.5% (w/w) acetic acid stock solution was added in a high shear mixer (Sonolator) at an approximate pH of 2.0 under high pressure to make the particles. Particles formed were wash in deionized water. It was found that diketopiperazine microparticles are not stable without the presence of a surfactant in the solutions, however, no surfactant was added to any of the solutions or reagents in making the particles.

In these experiments, using a dual-feed high shear mixer, equal masses of about 10.5 wt % acetic acid and about 2.5 wt % FDKP solutions at about 16° C.± about 2° C. were fed at 2000 psi through a 0.001-in$^2$ orifice to form a precipitate by homogenization. The precipitate was collected in a deionized (DI) water reservoir of about equal mass and temperature. The precipitate was concentrated and washed by tangential flow filtration with deionized water. The suspension can be finally concentrated to about less than 5% solids, for example, from about 2 to 3.5% based on the initial mass of FDKP. The concentrated suspension can be assayed for solids content by an oven drying method. For samples containing the active ingredients, i.e., insulin and/or GLP-1, a suspension of FDKP from above was used to which an insulin stock solution (insulin dissolved in 2% acetic acid was added to the suspension while mixing, then the suspension pH was titrated with ammonium hydroxide to pH 4.5±0.3. Similarly, a GLP-1 dissolved in a 2% acetic acid stock solution was added gravimetrically with stirring to an FDKP-suspension. The GLP-1 FDKP suspension was titrated to pH 4.5±0.1. Each of the insulin-FDKP suspension and GLP-1-FDKP suspension were independently dispersed using an external mixing 2-fluid nozzle into a Niro SD-Micro™ Spray Dryer fitted with a high efficiency cyclone. Nitrogen was used as the process gas (25 kg/h) and the atomization fluid (2.8 kg/hr). Samples were processed using two processing conditions in the spray dryer which are listed in Table 3.

TABLE 3

| Sample ID | inlet T (° C.) | outlet T (° C.) | atomization P (bar) | ΔT (° C.) | % solids in feed | feed rate (g/min) | inlet flow (kg/hr) | atz flow (kg/hr) | % yield |
|---|---|---|---|---|---|---|---|---|---|
| 100 | 130 | 75 | 3.0 | 55 | 3.58 | 7.13 | 25 | 2.8 | 88.4 |
| 103 | 130 | 75 | 4.0 | 55 | 3.31 | 7.39 | 25 | 2.8 | 83.9 |

For control samples, blank FDKP microcrystalline particles were manufactured identically minus the insulin or GLP-1 loading step.

FIG. 3 shows data from the experiment above wherein the feed solutions were free of surfactant. FIG. 3 is a graph illustrating the particle size distribution of a particle suspension of FDKP which exhibits a typical bimodal size distribution of the particles. The particles sizes herein range from about 0.1 to about 10 μm in diameter with one population of particles being centered at 0.2 μm in diameter and the other particle population centered at 2.1 μm in diameter.

Figure 4:
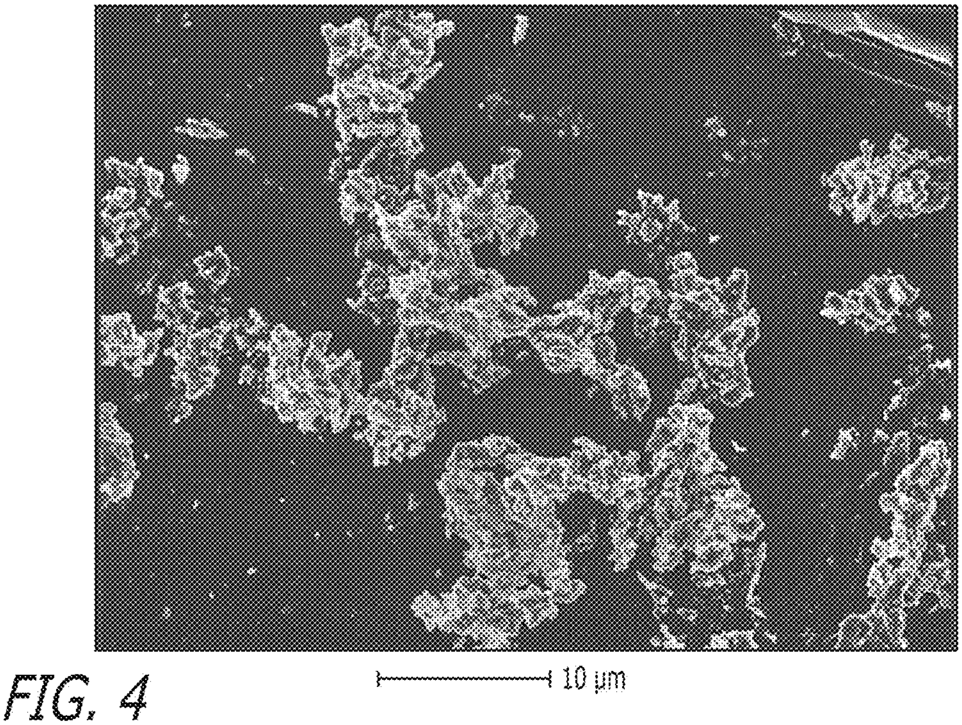
FIG. 4 depicts an SEM at low magnification (2500×) of FDKP particles recovered from an embodiment herein wherein a surfactant-free particle suspension is lyophilized.

Samples of the suspensions were lyophilized and not spray-dried. FIG. 4 is an SEM at 2,500× magnification of lyophilized particles. As seen in FIG. 4, upon lyophilization of a similar suspension, large flake-like particles were formed and gave a much larger average size when re-suspended in water as seen in FIG. 5. FIG. 5 shows the particle size distribution in suspension of a sample which was freeze-dried from particles made without the use of a surfactant. In this study, the particle size diameter of the resuspended particles increased from about 1 to about 90 μm or more.

Figure 7:
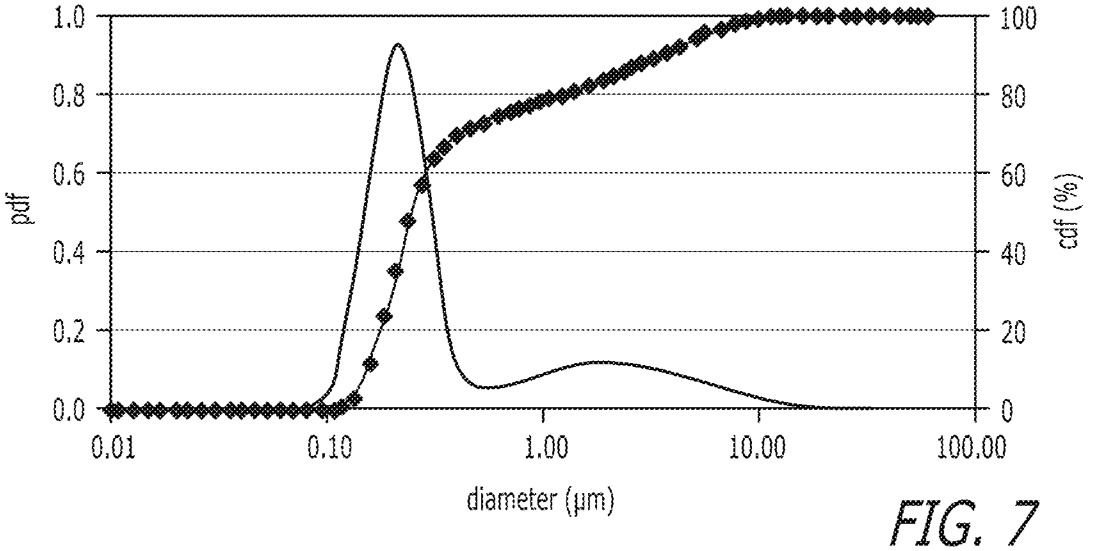
FIG. 7 depicts a graphic representation of particle size distribution of spray-dried surfactant-free particles dispersed in water.
Figure 8:
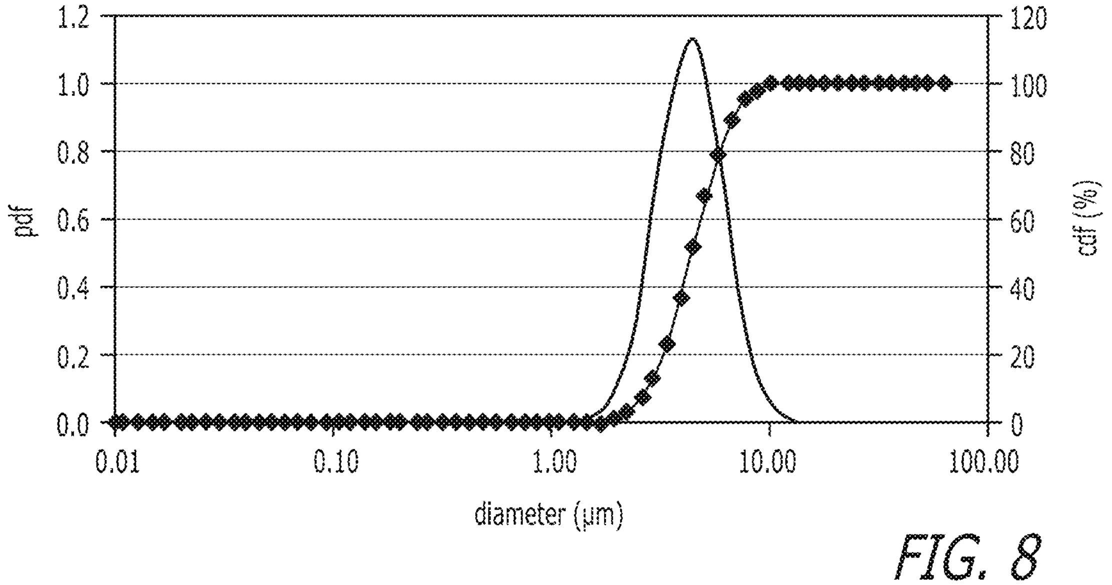
FIG. 8 depicts a graphic representation of the particle size distribution of spray-dried surfactant-free particles dispersed in 0.01 M HCl (pH 2).

FIG. 6 shows a typical 2,500× magnification of a scanning electron micrograph of powder sample from a surfactant-free preparation of microcrystalline FDKP particles which was formed using the present method and spray-dried as described above. As seen in FIG. 6 the particles are homogeneously spherical in structure comprising a shell of crystallites. When the surfactant-free suspension was spray-dried, particles with a physical diameter of approximately 4 μm were formed as shown in FIG. 6. Unlike standard FDKP particles, these particles dissociated into particles 0.2 μm in diameter when dispersed in water as shown in FIG. 7. Therefore, it is demonstrated that surfactants have a role in particle integrity. Dispersing the particles in 0.01 M hydrochloric acid inhibited particle dissociation as demonstrated in FIG. 8. It is possible that dissolved FDKP precipitates during spray drying and can be deposited along the boundaries between primary particles and can act as cement. The FDKP "cement" dissolves in water and the particles dissociate into the 0.2 μm primary particles; the lower solubility of FDKP in acid prevents dissolution and preserves particle integrity.

Example 2

Figure 9:
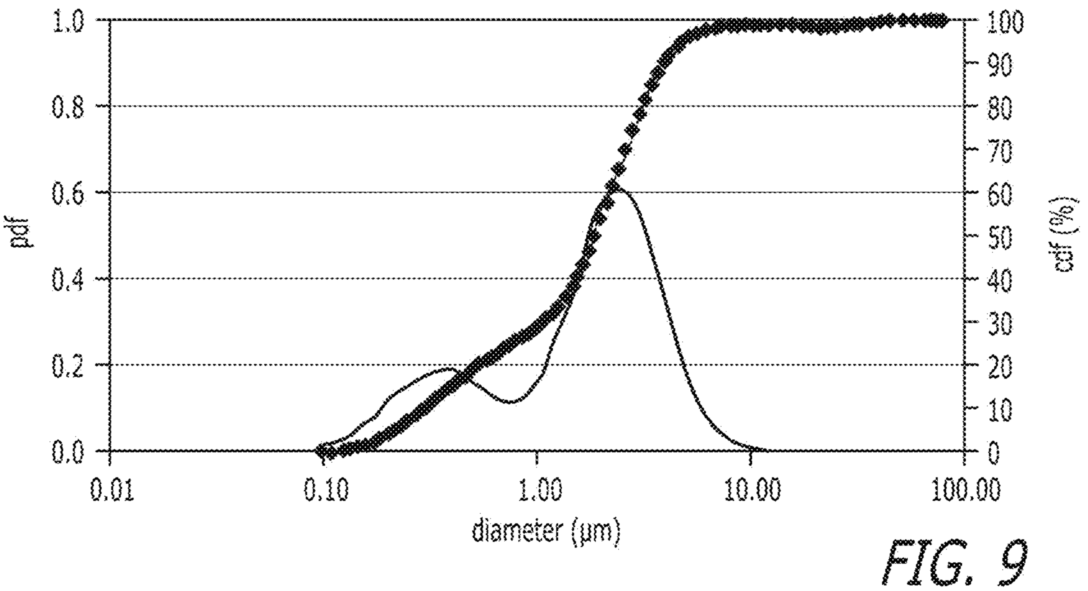
FIG. 9 depicts a graphic representation of the bimodal particle size distribution of a suspension formed by crystallizing $Na_2FDKP$ with acetic acid in the presence of surfactant.
Figure 10A:
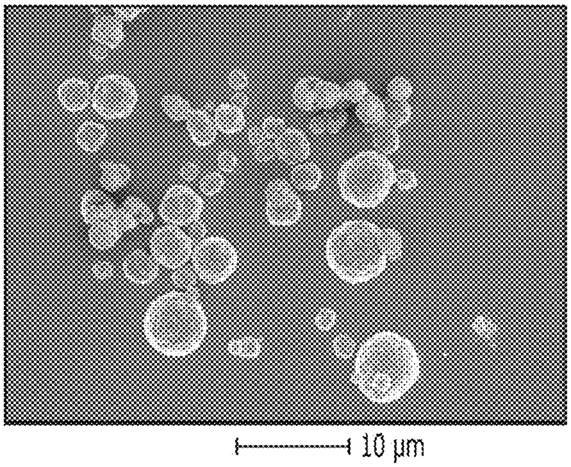
FIGS. 10A and 10B depict two scanning electron micrographs of particles prepared by spray drying the suspension of crystals prepared from $Na_2FDKP$ at 2,500× (10A) and 10,000× (10B) magnifications.
Figure 10B:
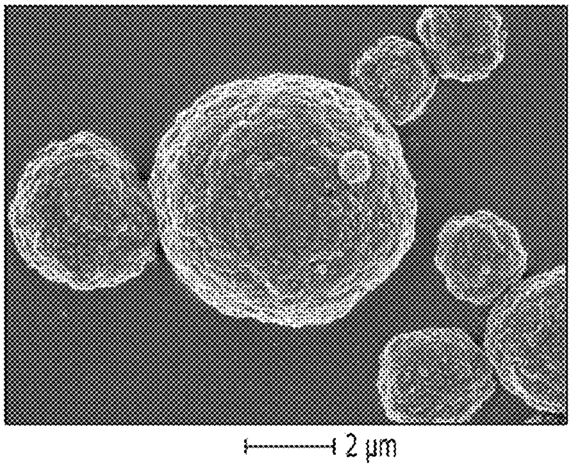

Manufacture of Microcrystalline FDKP Particles by Alternate Process Using a Diketopiperazine Salt Alternatively, crystallites of FDKP can be formed from feed solutions that contain surfactant. A feed solution of FDKP was prepared by dissolving the disodium salt of FDKP ($Na_2FDKP$) in water containing polysorbate 80 (PS80) as a surfactant without the use of ammonia as a reagent. A feed solution containing acetic acid (10.5% w/w), and PS80 (0.5% w/w) was also prepared. Mixing the two feed solutions in a DUAL FEED SONOLATOR crystallized the FDKP and yielded the bimodal particle size distribution illustrated in FIG. 9. As shown in FIG. 9, approximately 26% primary crystals formed were about 0.4 μm in diameter and about 74% of the larger particles have a diameter of about 2.4 μm. This suspension was processed and spray-dried to obtain particles and observed under SEM. The SEM micrographs were taken at 2,500× and 10,000× magnification and presented in FIGS. 10A and 10B. FIGS. 10A and 10B show that the particles are similar and spherical in shape, but smaller than those shown in FIG. 6 of Example 1, which particles were made using the FDKP as free acid. Table 4 below shows some of the physical characteristics measured for a powder made by lyophilization and a powder made by spray-drying (SD) using FDKP disodium salt.

TABLE 4

| process | % RF/fill | % CE | Bulk density g/mL | Tap density g/mL | SSA ($m^2/g$) |
|---|---|---|---|---|---|
| Lyophilized | 28.0 | 83.8 | 0.019 | 0.030 | 59.9 |
| SD | 62.8 | 88.2 | 0.159 | 0.234 | 49.6 |

The data show that the powder made from spray-dried particles exhibited higher respirable fraction (62.8 vs. 28%), higher cartridge emptying (% CE, 88.2% vs. 83.8%), and higher bulk (0.159 g/mL) and tap (0.234 g/mL) densities than the lyophilized powder (0.019 and 0.03 g/mL, respectively).

Example 3

Manufacture of Microcrystalline FDKP Particles Containing an Active Agent

Figure 11A:
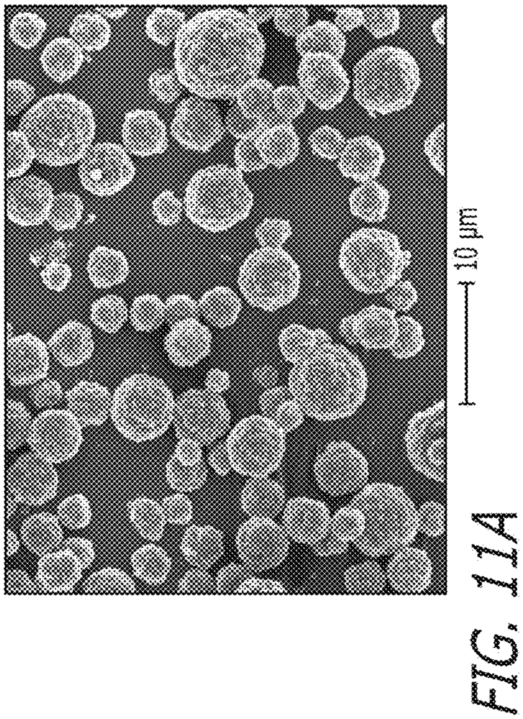
FIGS. 11A and 11B depict scanning electron micrographs of spray-dried surfactant-free FDKP particles with approximately 10 wt % insulin at 2,500× (11A) and at 5,000× (11B) magnifications.
Figure 11B:
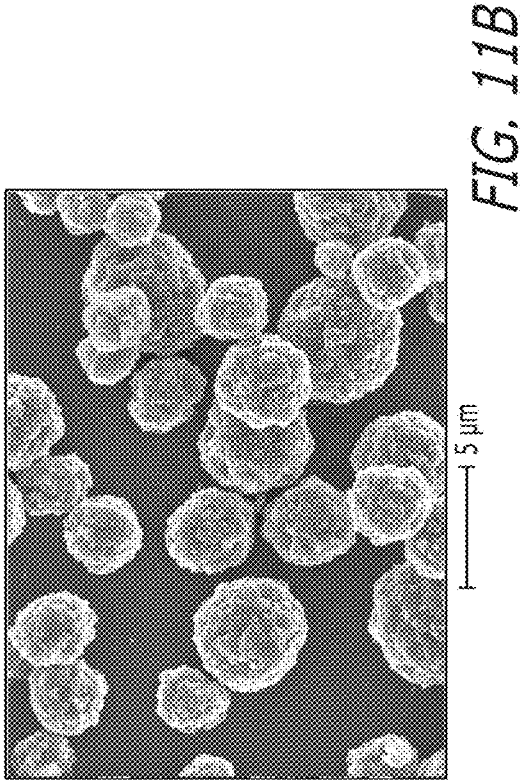

An active pharmaceutical ingredient (active agent) was incorporated into the particles by adding a solution of active agent to a suspension of surfactant-free FDKP crystallites and then spray drying the mixture to remove solvent as described in Example 1. Control particles (FDKP-insulin) were also made by the standard, self-assembly method using PS-80 in the solutions to make powder for pulmonary inhalation. In this study, insulin was dissolved in dilute acetic acid and added to a suspension of surfactant-free crystallites of FDKP (Samples 1 and 2 Table 5) prepared as in Example 1. The suspension was spray-dried to obtain a dry powder containing approximately 10 wt % insulin. Samples of the powders were taken for various analyses including delivery through a high resistance inhaler and scanning electron microscopy and the results are shown in Table 5. The particles were approximately the same size as the particles without insulin (Example 1) and the morphology of the particles (FIG. 11) was the same as those of FIG. 6. Moreover, both Samples 1 and 2 were less dense powder than the standard particles and Sample 1 particles have larger specific surface area (SSA) than the control. The distribution of insulin is not known, there are no obvious depositions of insulin on the particle surface to suggest the insulin is in the particle interior or incorporated into the particle wall.

TABLE 5

| Sample ID | % Insulin | % RF on Fill | % CE | SSA ($m^2/g$) | Bulk Density ($g/cm^3$) | Tapped Density ($g/cm^3$) |
|---|---|---|---|---|---|---|
| Control | 11.4 | 50 | 85 | 30-50 | 0.1 | 0.18 |
| 1 | 11.4 | 20.3 | 96.4 | 58.66 | 0.020 | 0.031 |
| 2 | 22.8 | 17.5 | 77.9 | 38.47 | 0.025 | 0.036 |

The data presented in Table 5, however, show that the surfactant-free powders behave differently from the standard particles at the same insulin content. For example, at the same insulin content the surfactant-free powder was released more effectively (96.4%) from the inhaler than the standard particle (85%). The increased in percent cartridge emptying (% CE) indicates that the powder has increased flowability.

The respirable fraction (% RF on Fill) was higher for the control particles as the inhaler used to test the powders was designed for the control powders.

Example 4

Figure 12A:
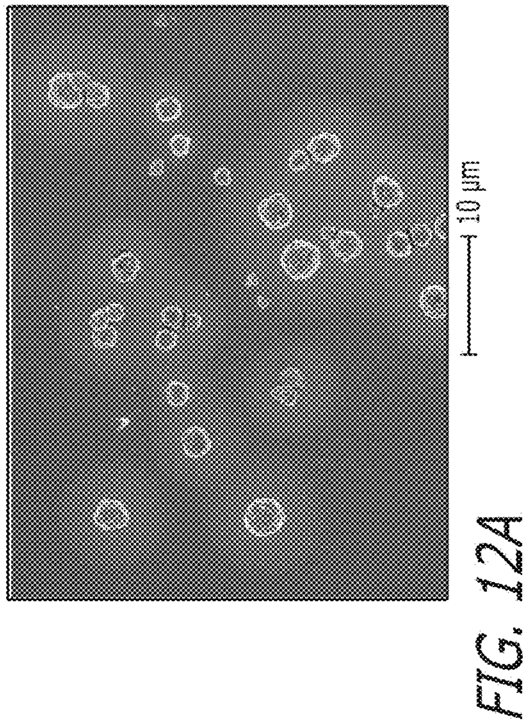
FIGS. 12A and 12B are two scanning electron micrographs of particles prepared by spray drying the suspension of crystals prepared from $Na_2DKP$ at 2,500× (12A) and at 10,000× (12B) magnification.
Figure 12B:
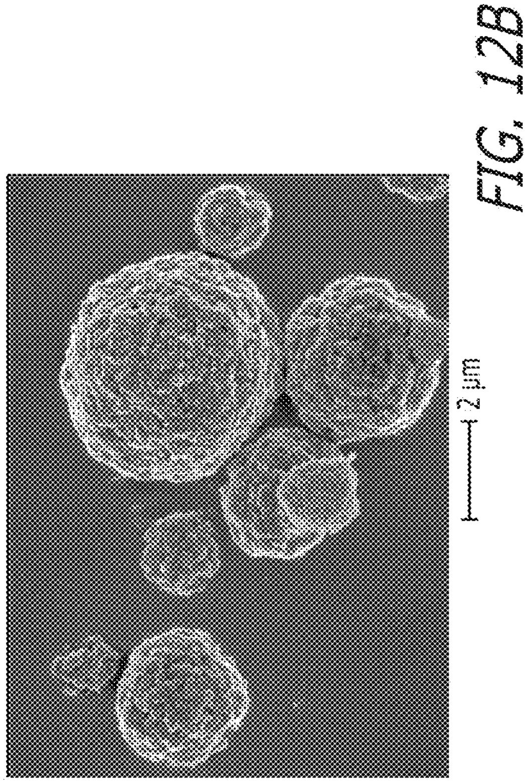
Figure 13:
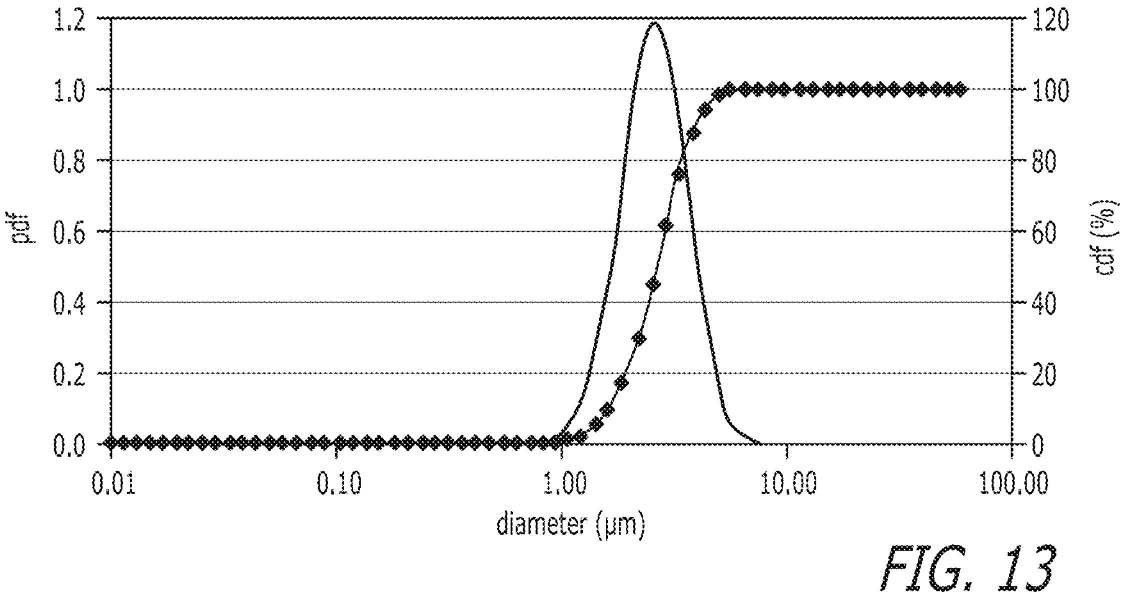
FIG. 13 depicts a graphic representation of the size distribution of particles formed by spray drying a suspension of FDKP crystallized from a solution of $Na_2FDKP$ and polysorbate 80. The particles were dispersed in water for the measurement.

Manufacture of Microcrystalline FDKP Particles by Alternate Process Using a Diketopiperazine Salt In this study, FDKP disodium salt was used to make an FDKP salt particle suspension as described in Example 2. An insulin solution was added to a suspension of surfactant-free microcrystals of FDKP prepared as in Example 2. The suspension was spray-dried to obtain a dry powder containing approximately 10 wt % insulin. The morphology of the particles formed is shown in the SEM at FIGS. 12A and 12B at 2,500× and 10,000× magnification (respectively). As seen in FIGS. 12A and 12B, the morphology was the same as the particles without insulin, showing a spherical shaped structure having a median diameter of the particles of 2.6 μm as shown in FIG. 13 and illustrated by the particles also ranging in diameter from about 1.0 μm to about 10 μm.

Example 5

Manufacture of Microcrystalline FDKP Particles Containing More Than One Active Agent In another embodiment, a composition comprising more than one active agent can be made using the present method. The method of making such composition comprises the steps as disclosed above for each individual active agent to form an active agent-FDKP suspension of each of the active agents to be incorporated into the composition. Then, the suspensions are combined and blended to form a mixture. Then the blended mixture is dispersed and spray-dried as described above to make the microcrystalline diketopiperazine particles comprising more than one active agent. In one exemplary study, insulin and GLP-1 combination powder was made.

Suspensions of FDKP crystallites prepared as in Example 1 were mixed with solutions of various active agents (e.g., ghrelin, low molecular heparin, oxyntomodulin) and spry dried to obtain particles similar in properties to those in Example 3.

Example 6

Manufacture of Microcrystalline FDKP Particles Containing Two Active Agents

Figure 14:
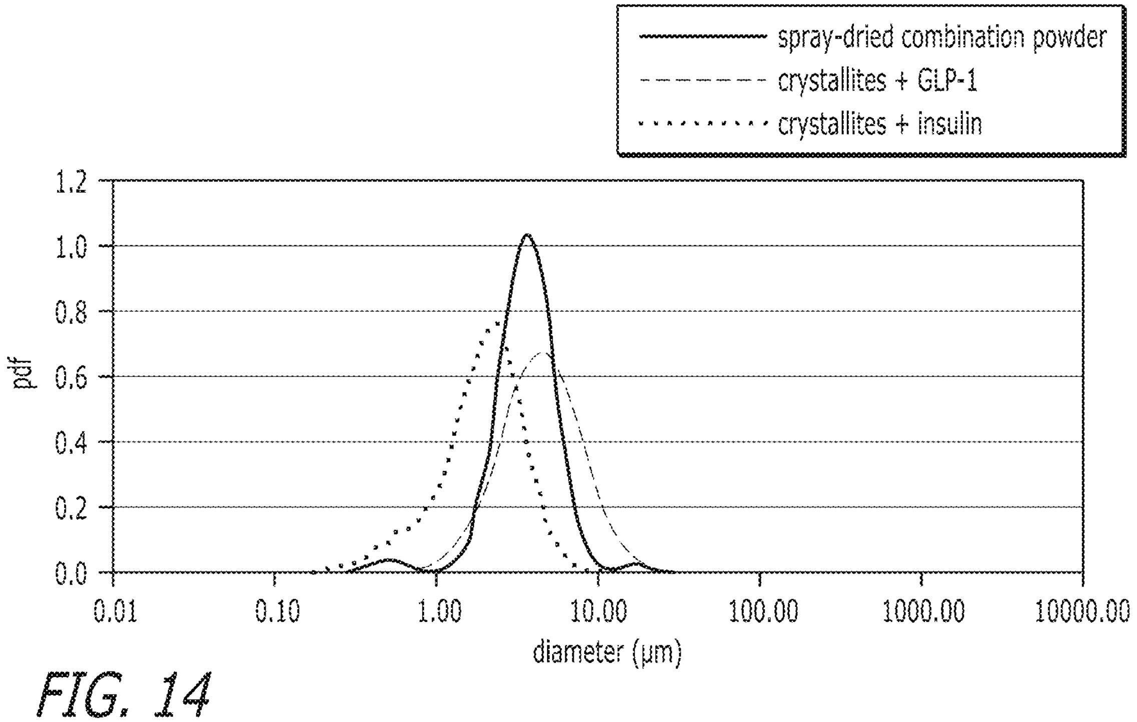
FIG. 14 depicts a graphic representation of the particle size distributions of a spray-dried combination powder and the crystallite suspension with the individual active agents. The number 1 represents the particle size distribution of the combined microcrystalline powder composition comprising two different active agents; in separate diketopiperazine-active agent particle suspension, wherein one composition contained particles of FDKP-GLP-1 and the other contained FDKP-insulin (3) in suspensions which were combined prior to being spray-dried.

A combination powder with two active agents (GLP-1 and insulin) was produced by first preparing a suspension of FDKP crystallites with insulin and a second suspension of crystallites with GLP-1. The two suspensions were then mixed and the combined suspension was spray-dried to obtain a dry powder containing both active agents. The crystallite suspensions were prepared as in Example 1; after the active agents were added, the suspension was adjusted to pH 4.5 to promote adsorption onto the crystallites. FIG. 14 is a plot of data illustrating the particle size distribution of the spray-dried combination powder (1) and the crystallite suspension with the individual active agents, FDKP-insulin (2) and FDKP-GLP-1.

As seen in FIG. 14, the particle size distribution of the combination powder was centered between those of the two individual suspensions and was significantly narrower. The combination powder comprised particles having a diameter of from about 1 μm to about 10 μm. The crystallites containing the insulin were smaller (from about 0.25 μm to about 10 μm) than the GLP-1 containing crystallites which have a diameter ranging from about 0.5 μm to about 50 μm. The atomization step in spray drying probably dissociates the original clusters of crystallites in suspension and reforms the particles with a size distribution that depends on the conditions in the suspension and spray-drying conditions.

Example 7

Administration of a Dry Powder Composition Comprising Crystalline Diketopiperazine Particles to a Subject Dry powder formulations comprising microcrystalline diketopiperazine microparticles made with the disodium salt of FDKP ($Na_2$FDKP) were made as described in Example 1 above to contain 9 U of insulin per milligram of composition. High resistance inhalers containing a cartridge (Dreamboat™ inhaler, MannKind Corporation) were prepared containing 1 mg to 10 mg per dose were prepared to administer to subjects diagnosed with diabetes. An inhaler containing an insulin dose is provided to the patient to be treated and the patient inhales the insulin dose in a single inhalation at the start, during a meal or thereafter a meal.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of making microcrystalline 3,6-bis(N-fumaryl-4-aminobutyl)-2,5-diketopiperazine particles suitable for pulmonary administration as a dry powder comprising:

adding 3,6-bis(N-fumaryl-4-aminobutyl)-2,5-diketopiperazine to a solution at an acidic pH to form a suspension of microcrystalline 3,6-bis(N-fumaryl-4-aminobutyl)-2,5-diketopiperazine particles having a bimodal distribution in particle sizes which range from about 0.05 μm to about 10 μm wherein a first peak of the microcrystalline diketopiperazine particles of the bimodal distribution in particle sizes has an average of about 0.2 μm to about 2.4 μm and a second peak of particles has an average size of about 2.1 μm to about 2.4 μm; adding a solution comprising one or more active ingredients to the suspension; washing said microcrystalline 3,6-bis(N-fumaryl-4-aminobutyl)-2,5-diketopiperazine particles formed in the suspension with deionized water; atomizing said suspension using a spray dryer under an air or gas stream; reforming said microcrystalline 3,6-bis(N-fumaryl-4-aminobutyl)-2,5-diketopiperazine particles by spray-drying into a dry powder comprising said 3,6-bis(N-fumaryl-4-aminobutyl)-2,5-diketopiperazine particles.

2. The method of claim 1, wherein the one or more active ingredients is a vasoactive agent.

3. The method of claim 1, further comprising the step of adding a surfactant to the solution or suspension.

4. The method of claim 3, wherein the surfactant is polysorbate 80.

5. The method of claim 1, wherein the one or more active ingredients is a peptide, a protein, a nucleic acid molecule, or a small organic molecule.

6. The method of claim 1, wherein the one or more active ingredients is a vasoactive agent, a neuroactive agent including opioid agonists and antagonists, a hormone, an anticoagulant, an immunomodulating agent, a cytotoxic agent, an antibiotic, an antiviral agent, an antigen, an infectious agent, an inflammatory mediator, a cell surface receptor agonist or antagonist, or a cell surface antigen.

7. The method of claim 1, wherein the one or more active ingredients is at least one of insulin or an analog thereof, a parathyroid hormone or an analog thereof, calcitonin, glucagon, glucagon-like peptide 1, oxyntomodulin, peptide YY, leptin, a cytokine, a lipokine, an enkephalin, a cyclosporin, an anti-IL-8 antibody, an IL-8 antagonist including ABX-IL-8; a prostaglandin including PG-I2, an LTB receptor blocker including LY2931 1, BIIL 284 and CP105696; a triptan such as sumatriptan or palmitoleate, a growth hormone or analogs thereof, a parathyroid hormone related peptide (PTHrP), ghrelin, obestatin, enterostatin, granulocyte macrophage colony stimulating factor (GM-CSF), amylin, amylin analogs, clopidogrel, PPACK (D-phenylalanyl-L-prolyl-L-arginine chloromethyl ketone), adiponectin, cholecystokinin (CCK), secretin, gastrin, motilin, somatostatin, brain natriuretic peptide (BNP), atrial natriuretic peptide (ANP), IGF-1, growth hormone releasing factor (GHRF), integrin beta-4 precursor (ITB4) receptor antagonist, analgesics, nociceptin, nocistatin, orphanin FQ2, CGRP, angiotensin, substance P, neurokinin A, a pancreatic polypeptide, a neuropeptide Y, a delta-sleep-inducing peptide, or a vasoactive intestinal peptide.

8. The method of claim 1, wherein one or more active ingredients comprise a prostaglandin, analog or derivative thereof.

9. The method of claim 8, wherein the prostaglandin, analog or derivative thereof is a PG-I2.

* * * * *